(12) United States Patent
Jukes et al.

(10) Patent No.: US 9,062,271 B2
(45) Date of Patent: Jun. 23, 2015

(54) PROCESS FOR PREPARING AN OVERBASED SALT OF A SULFURIZED ALKYL-SUBSTITUTED HYDROXYAROMATIC COMPOSITION

(71) Applicants: Ronald T. F. Jukes, Rotterdam (NL); Eugene E. Spala, Fairfield, CA (US)

(72) Inventors: Ronald T. F. Jukes, Rotterdam (NL); Eugene E. Spala, Fairfield, CA (US)

(73) Assignees: Chevron Oronite Technology B.V., Rotterdam (NL); Chervon Oronite Company LLC, San Ramon, CA (US)

( * ) Notice: Subject to any disclaimer, the term of this patent is extended or adjusted under 35 U.S.C. 154(b) by 0 days.

(21) Appl. No.: 14/067,121

(22) Filed: Oct. 30, 2013

(65) Prior Publication Data

US 2015/0119304 A1 Apr. 30, 2015

(51) Int. Cl.
*C10M 159/22* (2006.01)
*C10M 135/02* (2006.01)
*C07C 319/14* (2006.01)

(52) U.S. Cl.
CPC ............ *C10M 135/02* (2013.01); *C07C 319/14* (2013.01)

(58) Field of Classification Search
USPC ......................................... 508/572, 573, 574
See application file for complete search history.

(56) References Cited

U.S. PATENT DOCUMENTS

| | | | |
|---|---|---|---|
| 3,036,003 A | 5/1962 | Verdol | |
| 3,172,892 A | 3/1965 | Le Suer et al. | |
| 3,219,666 A | 11/1965 | Norman et al. | |
| 3,272,746 A | 9/1966 | Le Suer et al. | |
| 3,275,554 A | 9/1966 | Wagenaar | |
| 3,329,658 A | 7/1967 | Fields | |
| 3,438,757 A | 4/1969 | Honnen et al. | |
| 3,449,250 A | 6/1969 | Fields | |
| 3,454,555 A | 7/1969 | Van Der Voort et al. | |
| 3,565,804 A | 2/1971 | Honnen et al. | |
| 3,586,629 A | 6/1971 | Otto et al. | |
| 3,591,598 A | 7/1971 | Traise et al. | |
| 3,666,730 A | 5/1972 | Coleman | |
| 3,953,538 A | 4/1976 | Boney | |
| 3,980,569 A | 9/1976 | Pindar et al. | |
| 4,225,737 A | 9/1980 | Mikulicz | |
| 4,234,435 A | 11/1980 | Meinhardt | |
| 4,328,111 A | 5/1982 | Watson et al. | |
| 4,536,301 A | 8/1985 | Malloy et al. | |
| 4,612,132 A | 9/1986 | Wollenberg et al. | |
| 4,746,446 A | 5/1988 | Wollenberg et al. | |
| 4,816,185 A | 3/1989 | Parker et al. | |
| 4,870,217 A | 9/1989 | Knifton | |
| 5,004,841 A | 4/1991 | Lee | |
| 5,468,407 A | 11/1995 | Frazier | |
| 5,716,912 A | 2/1998 | Harrison et al. | |
| 5,750,818 A | 5/1998 | Mehlberg et al. | |
| 6,054,419 A | 4/2000 | Le Coent | |
| 6,165,235 A | 12/2000 | Kolp et al. | |
| 6,372,696 B1 | 4/2002 | Tipton | |
| 6,440,905 B1 | 8/2002 | Epps et al. | |
| 6,551,967 B2 | 4/2003 | King et al. | |
| 6,989,355 B1 | 1/2006 | Campbell et al. | |
| 8,772,209 B2 * | 7/2014 | Mahieux et al. | ............ 508/574 |
| 2007/0265476 A1 | 11/2007 | Dakka et al. | |
| 2008/0070818 A1 | 3/2008 | Arrowsmith et al. | |
| 2009/0143264 A1 | 6/2009 | Harrison et al. | |

* cited by examiner

*Primary Examiner* — Sudhakar Katakam
*Assistant Examiner* — Pancham Bakshi

(57) ABSTRACT

Disclosed herein is an overbased salt of a sulfurized alkyl-substituted hydroxyaromatic composition, which is prepared by the process comprising (a) providing an overbased salt of a sulfurized alkyl-substituted hydroxyaromatic composition having a total base number (TBN) greater than about 250; and (b) sparging the overbased salt of a sulfurized alkyl-substituted hydroxyaromatic composition with air at a temperature ranging from about 190° C. to about 250° C.

9 Claims, No Drawings

PROCESS FOR PREPARING AN OVERBASED SALT OF A SULFURIZED ALKYL-SUBSTITUTED HYDROXYAROMATIC COMPOSITION

BACKGROUND OF THE INVENTION

1. Technical Field

The present invention generally relates to a process for preparing an overbased salt of a sulfurized alkyl-substituted hydroxyaromatic composition.

2. Description of the Related Art

The lubricant additive industry generally uses alkyl phenols (e.g., tetrapropenyl phenol, TPP) to prepare detergents comprising sulfurized metal alkyl phenates. Metal salts of sulfurized alkylphenols are useful lubricating oil additives which impart detergency and dispersancy properties to the lubricating oil composition for marine, automotive, railroad and air-cooled engines as well as providing for an alkalinity reserve in the oil. Alkalinity reserve is necessary in order to neutralize acids generated during engine operation. Without this alkalinity reserve, the acids so generated would result in harmful engine corrosion.

In the not so distant past, rapidly escalating energy costs, particularly those incurred in distilling crude oil and liquid petroleum, became burdensome to the users of transportation fuels, such as owners and operators of seagoing ships. In response, those users have steered their operations away from steam turbine propulsion units in favor of large marine diesel engines that are more fuel efficient. Diesel engines may generally be classified as slow-speed, medium-speed, or high-speed engines, with the slow-speed variety being used for the largest, deep shaft marine vessels and certain other industrial applications.

Slow-speed diesel engines are unique in size and method of operation. The engines themselves are massive, the larger units may approach 200 tons in weight and an upward of 10 feet in length and 45 feet in height. The output of these engines can reach as high as 100,000 brake horsepower with engine revolutions of 60 to about 200 revolutions per minute. They are typically of crosshead design and operate on the two-stroke cycle.

Medium-speed engines, on the other hand, typically operate in the range of about 250 to about 1100 rpm and may operate on either the four-stroke or the two-stroke cycle. These engines can be of trunk piston design or occasionally of crosshead design. They typically operate on residual fuels, just like the slow-speed diesel engines, but some may also operate on distillate fuels that contain little or no residue. These engines can also be used for propulsion, ancillary applications or both on deep-sea vessels.

Slow- and medium-speed diesel engines are also extensively used in power plant operations. A slow- or medium-speed diesel engine that operates on the 2-stroke cycle is typically a direct-coupled and direct-reversing engine of crosshead construction, with a diaphragm and one or more stuffing boxes separating the power cylinders from the crankcase to prevent combustion products from entering the crankcase and mixing with the crankcase oil. The notable complete separation of the crankcase from the combustion zone has led persons skilled in the art to lubricate the combustion chamber and the crankcase with different lubricating oils.

Accordingly, in large diesel engines of the crosshead type used in marine and heavy stationary applications, the cylinders are lubricated separately from the other engine components. The cylinders are lubricated on a total loss basis with the cylinder oil being injected separately to quills on each cylinder by means of lubricators positioned around the cylinder liner. Oil is distributed to the lubricators by means of pumps, which are, in modern engine designs, actuated to apply the oil directly onto the rings to reduce wastage of the oil.

The high stresses encountered in these engines and the use of residual fuels creates the need for lubricants with a high detergency and neutralizing capability even though the oils are exposed to thermal and other stresses only for short periods of time. Residual fuels commonly used in these diesel engines typically contain significant quantities of sulfur, which, in the combustion process, combine with water to form sulfuric acid, the presence of which leads to corrosive wear. In particular, in two-stroke engines for ships, areas around the cylinder liners and piston rings can be corroded and worn by the acid. Therefore, it is important for diesel engine lubricating oils to have the ability to resist such corrosion and wear.

Accordingly, a primary function of marine cylinder lubricants is to neutralize sulfur-based acidic components of high-sulfur fuel oil combusted in slow-speed 2-cycle crosshead diesel engines. This neutralization is accomplished by the inclusion in the marine cylinder lubricant of basic species such as metallic detergents, e.g., sulfurized metal alkyl phenates. Unfortunately the basicity of the marine cylinder lubricant can be diminished by oxidation of the marine cylinder lubricant (caused by the thermal and oxidative stress the lubricant undergoes in the engine), thus decreasing the lubricant's neutralization ability. The oxidation can be accelerated if the marine cylinder lubricants contain oxidation catalysts such as wear metals that are generally known to be present in the lubricant during engine operation.

Medium-speed trunk piston engines typically operate using various types and qualities of diesel fuels and heavy fuel oils. These engines are lubricated with trunk piston engine oils which are required to have the ability to form a protective layer between moving surfaces, neutralize acids, and keep contaminants suspended in the oil. Unfortunately, these properties can be adversely affected by oxidation of the oil resulting in viscosity increase, loss of neutralization capacity and loss of detergency. Accordingly, there is a need for improved detergents such as sulfurized metal alkyl phenates which provide better oxidative stability to a lubricating oil composition such as marine diesel engine lubricating oil compositions, e.g., marine cylinder lubricants and trunk piston engine oils.

The lubricant additive industry generally uses alkyl phenols (e.g., tetrapropenyl phenol, TPP) to prepare detergents comprising sulfurized metal alkyl phenates. Metal salts of sulfurized alkylphenols are useful lubricating oil additives which impart detergency and dispersancy properties to the lubricating oil composition for marine, automotive, railroad and air-cooled engines as well as providing for an alkalinity reserve in the oil. Alkalinity reserve is necessary in order to neutralize acids generated during engine operation. Without this alkalinity reserve, the acids so generated would result in harmful engine corrosion. However, there may be some unreacted alkyl phenols such as tetrapropenyl phenol present in the sulfurized metal alkyl phenate as well as in lubricating oils containing one or more of the sulfurized metal alkyl phenates.

A recent reproductive toxicity study in rats sponsored by the Petroleum Additives Panel of the American Chemistry Council shows that free or unreacted TPP may cause adverse effects on male and female reproductive organs. Further, it is believed that TPP may be corrosive or irritating to the skin.

U.S. Patent Application Publication No. 20080070818 ("the '818 publication") discloses a lubricating oil composition including at least one sulfurized overbased metal phenate detergent prepared from a $C_9$-$C_{15}$ alkyl phenol, at least one sulfurizing agent, at least one metal and at least one overbasing agent; the detergent including less than 6.0% by combined mass of unsulfurized $C_9$-$C_{15}$ alkyl phenol and unsulfurized metal salts thereof.

U.S. Patent Application Publication No. 20090143264 ("the '264 publication") discloses sulfurized metal alkyl phenate compositions having a low alkyl phenol content. The sulfurized metal alkyl phenate compositions of the '264 publication can be prepared by reacting a phenol compound such as tetrapropenyl phenol with an aldehyde to form a phenolic resin and then reacting the phenolic resin simultaneously with a metal base and a first sulfurizing agent.

U.S. Pat. No. 4,328,111 ("the '111 patent") discloses that overbased phenates, including sulfurized phenates are commonly manufactured in the presence of ethylene glycol which is difficult to remove from the product, thereby wasting raw materials and sometimes leading to undesirable side effects from glycol in the final product. The '111 patent further discloses that in order to remove ethylene glycol, an acidic compound is reacted with a basic compound comprising an overbased metal sulfonate, phenate, or mixtures thereof, and the reaction product is then nitrogen stripped to remove the ethylene glycol.

A need still remains, therefore, for an improved overbased salt of a sulfurized alkyl-substituted hydroxyaromatic composition having oxidative stability in a lubricating oil composition such as, for example, a marine diesel engine lubricating oil composition. In addition, to reduce any potential health risks to customers and to avoid potential regulatory issues, there is a need to reduce the amount of free unsulfurized alkyl-substituted hydroxyaromatic compound and its metal salt in the salt of a sulfurized alkyl-substituted hydroxyaromatic composition in a simple, cost efficient manner. Accordingly, it is also desirable to provide an improved process for preparing a salt of a sulfurized alkyl-substituted hydroxyaromatic composition which has relatively low levels of unsulfurized alkyl substituted hydroxyaromatic compound and its metal salt.

SUMMARY OF THE INVENTION

In accordance with one embodiment of the present invention, there is provided a process for preparing an overbased salt of a sulfurized alkyl-substituted hydroxyaromatic composition comprising:
(a) providing an overbased salt of a sulfurized alkyl-substituted hydroxyaromatic composition having a total base number greater than about 250; and
(b) sparging the overbased salt of a sulfurized alkyl-substituted hydroxyaromatic composition with air at a temperature ranging from about 190° C. to about 250° C.

In accordance with a second embodiment of the present invention, there is provided an overbased salt of a sulfurized alkyl-substituted hydroxyaromatic composition which is prepared by the process comprising:
(a) providing an overbased salt of a sulfurized alkyl-substituted hydroxyaromatic composition having a total base number greater than about 250; and
(b) sparging the overbased salt of a sulfurized alkyl-substituted hydroxyaromatic composition with air at a temperature ranging from about 190° C. to about 250° C.

In accordance with a third embodiment of the present invention, there is provided a lubricating oil composition comprising:
(a) a major amount of an oil of lubricating viscosity; and
(b) a minor amount of an overbased salt of a sulfurized alkyl-substituted hydroxyaromatic composition which is prepared by the process comprising:
(i) providing an overbased salt of a sulfurized alkyl-substituted hydroxyaromatic composition having a total base number greater than about 250; and
(ii) sparging the overbased salt of a sulfurized alkyl-substituted hydroxyaromatic composition with air at a temperature ranging from about 190° C. to about 250° C.

In accordance with a fourth embodiment of the present invention, there is provided a method for improving oxidative stability of a lubricating oil composition used in an internal combustion engine, the method comprising adding a minor amount of an overbased salt of a sulfurized alkyl-substituted hydroxyaromatic composition to a lubricating oil composition comprising a major amount of an oil of lubricating viscosity, wherein the overbased salt of a sulfurized alkyl-substituted hydroxyaromatic composition is prepared by the process comprising:
(a) providing an overbased salt of a sulfurized alkyl-substituted hydroxyaromatic composition having a total base number greater than about 250; and
(b) sparging the overbased salt of a sulfurized alkyl-substituted hydroxyaromatic composition with air at a temperature ranging from about 190° C. to about 250° C.

In accordance with a fifth embodiment of the present invention, there is provided a use of an overbased salt of a sulfurized alkyl-substituted hydroxyaromatic composition which is prepared by the process comprising:
(a) providing an overbased salt of a sulfurized alkyl-substituted hydroxyaromatic composition having a total base number greater than about 250; and
(b) sparging the overbased salt of a sulfurized alkyl-substituted hydroxyaromatic composition with air at a temperature ranging from about 190° C. to about 250° C., for improving oxidative stability of a lubricating oil composition used in an internal combustion engine.

Among other factors, the present invention is based on the surprising discover that an overbased salt of a sulfurized alkyl-substituted hydroxyaromatic composition alkyl-substituted hydroxyaromatic composition prepared by the process described herein advantageously and unexpectedly provides a resulting composition which is substantially free of the unsulfurized alkyl-substituted hydroxyaromatic compound and the unsulfurized metal salt of the alkyl-substituted hydroxyaromatic compound, as well as improves the oxidative stability of a lubricating oil composition as compared to an overbased salt of a sulfurized alkyl-substituted hydroxyaromatic composition having a total base number greater than about 250; and not subjected to the step of sparging the overbased salt of a sulfurized alkyl substituted hydroxyaromatic composition with air at a temperature ranging from about 190° C. to about 250° C. By having the overbased salt of a sulfurized alkyl-substituted hydroxyaromatic composition having improved antioxidancy, the lifetime of the oil can be increased while reducing deposit formation in the engine.

DETAILED DESCRIPTION OF THE PREFERRED EMBODIMENTS

Prior to discussing the invention in further detail, the following terms will be defined:

Definitions

As used herein, the following terms have the following meanings, unless expressly stated to the contrary:

The term "Total Base Number" or "TBN" as used herein refers to the amount of base equivalent to milligrams of KOH in 1 gram of sample. Thus, higher TBN numbers reflect more alkaline products, and therefore a greater alkalinity reserve. The TBN of a sample can be determined by ASTM Test No. D2896-11 issued May 15, 2011 or any other equivalent procedure.

The term "phenate" means a metal salt of a phenol.

The term "alkylphenate" means a metal salt of an alkylphenol.

The term "alkylphenol" means a phenol having one or more alkyl substituents, wherein at least one of the alkyl substituents has a sufficient number of carbon atoms to impart oil solubility to the phenol.

The term "lime" refers to calcium hydroxide, also known as slaked lime or hydrated lime.

The term "metal" means alkali metals, alkaline earth metals, or mixtures thereof.

The term "alkaline earth metal" refers to calcium, barium, magnesium, and strontium.

The term "alkali metal" refers to lithium, sodium potassium, rubidium, and cesium.

The term "metal base" refers to a metal hydroxide, metal oxide, metal alkoxides and the like and mixtures thereof, wherein the metal is an alkaline earth metal or alkali metal.

The term "overbased" refers to a class of metal salts or complexes. These materials have also been referred to as "basic", "superbased", "hyperbased", "complexes", "metal cornplexes", "high-metal containing salts", and the like. Overbased products are metal salts or complexes characterized by a metal content in excess of that which would be present according to the stoichiometry of the metal and the particular acidic organic compound reacted with the metal, e.g., a carboxylic acid. Suitable overbasing metals include alkaline earth metals such as magnesium, calcium, barium, and strontium. Suitable overbasing metals can be provided from the corresponding metal hydroxides, for example, calcium hydroxide and magnesium hydroxide provide the source for the alkaline earth metals calcium and magnesium, respectively. Additional overbasing can be achieved by the addition of acidic overbasing compounds for example, carbon dioxide and boric acid.

The term "sulfated ash content" refers to the amount of metal-containing additives (e.g., calcium, magnesium, molybdenum, zinc, etc.) in a lubricating oil composition and is typically measured according to ASTM D874-07, which is incorporated herein by reference.

The present invention is directed to an overbased salt of a sulfurized alkyl-substituted hydroxyaromatic composition which is prepared by the process comprising: (a) providing an overbased salt of a sulfurized alkyl-substituted hydroxyaromatic composition having a total base number greater than about 250; and (b) sparging the overbased salt of a sulfurized alkyl-substituted hydroxyaromatic composition with air at a temperature ranging from about 190° C. to about 250° C.

Salt of a Sulfurized Alkyl-substituted Hydroxyaromatic Composition

In general, an overbased salt of a sulfurized alkyl-substituted hydroxyaromatic composition having a total base number greater than about 250 is obtained by (i) alkylating a hydroxyaromatic compound with an alkylating agent such as one or more olefins comprising $C_9$ to $C_{18}$ oligomers of monomers selected from propylene, butylene or mixtures thereof, to provide an alkyl-substituted hydroxyaromatic compound; and (ii) sulfurizing, neutralizing and overbasing the alkyl-substituted hydroxyaromatic compound in any order to provide an overbased salt of a sulfurized alkyl-substituted hydroxyaromatic composition having a total base number greater than about 250.

The alkyl-substituted hydroxyaromatic compound employed in the present invention is prepared by methods that are well known in the art. Useful hydroxyaromatic compounds that may be alkylated include mononuclear monohydroxy and polyhydroxy aromatic hydrocarbons having 1 to 4, and preferably 1 to 3, hydroxyl groups. Suitable hydroxyaromatic compounds include phenol, catechol, resorcinol, hydroquinone, pyrogallol, cresol, and the like and mixtures thereof. In one embodiment, the hydroxyaromatic compound is a phenol.

In general, the alkylating agent employed to alkylate the hydroxyaromatic compound includes alpha olefins having from about 10 to about 80 carbon atoms. The olefins employed may be linear, isomerized linear, branched or partially branched linear. The olefin may be a mixture of linear olefins, a mixture of isomerized linear olefins, a mixture of branched olefins, a mixture of partially branched linear or a mixture of any of the foregoing.

In one embodiment, the mixture of linear olefins that may be used is a mixture of normal alpha olefins selected from olefins having from about 12 to about 30 carbon atoms per molecule. In one embodiment, the normal alpha olefins are isomerized using at least one of a solid or liquid catalyst.

In another embodiment, the olefins are a branched olefinic propylene oligomer or mixture thereof having from about 20 to about 80 carbon atoms, i.e., branched chain olefins derived from the polymerization of propylene. The olefins may also be substituted with other functional groups, such as hydroxy groups, carboxylic acid groups, heteroatoms, and the like. In one embodiment, the branched olefinic propylene oligomer or mixtures thereof have from about 20 to about 60 carbon atoms. In one embodiment, the branched olefinic propylene oligomer or mixtures thereof have from about 20 to about 40 carbon atoms.

In another embodiment, the alkylating agent employed to alkylate the hydroxyaromatic compound includes one or more olefins comprising $C_9$ to $C_{18}$ oligomers of monomers selected from propylene, butylene or mixtures thereof. Generally, the one or more olefins will contain a major mount of the $C_9$ $C_{18}$ oligomers of monomers selected from propylene, butylene or mixtures thereof. Examples of such olefins include propylene tetramer, butylene trimer and the like. As one skilled in the art will readily appreciate, other olefins may be present. For example, the other olefins that can be used in addition to the $C_9$ to $C_{18}$ oligomers include linear olefins, cyclic olefins, branched olefins other than propylene oligomers such as butylene or isobutylene oligomers, arylalkylenes and the like and mixtures thereof. Suitable linear olefins include 1-hexane, 1-nonene, 1-decene, 1-dodecene and the like and mixtures thereof. Especially suitable linear olefins are high molecular weight normal alpha-olefins such as $C_{16}$ to $C_{30}$ normal alpha-olefins, which can be obtained from processes such as ethylene oligomerization or wax cracking. Suitable cyclic olefins include cyclohexene, cyclopentene, cyclooctene and the like and mixtures thereof. Suitable branched olefins include butylene dimer or trimer or higher molecular weight isobutylene oligomers, and the like and mixtures thereof. Suitable arylalkylenes include styrene, methyl styrene, 3-phenylpropene, 2-phenyl-2-butene and the like and mixtures thereof.

Alkylation of the hydroxyaromatic compound with the alkylating agent is generally carried out in the presence of an alkylation catalyst. Useful alkylation catalysts include Lewis acid catalysts, solid acid catalysts, trifluoromethanesulfonic acid, and acidic molecular sieve catalysts. Suitable Lewis acid catalysts include aluminum trichloride, aluminum tribromide, aluminum triiodide, boron trifluoride, boron tribromide, boron triiodide and the like.

Suitable solid acidic catalysts include zeolites, acid clays, and/or silica-alumina. The catalyst may be a molecular sieve. Eligible molecular sieves are silica-aluminophosphate molecular sieves or metal silica-aluminophosphate molecular sieves, in which the metal may be, for example, iron, cobalt or nickel. In one embodiment, a solid catalyst is a cation exchange resin in its acid form, for example, crosslinked sulfonic acid catalyst. Suitable sulfonated acidic ion exchange resin type catalysts include Amberlyst 36®, available from Dow Chemical Co. The acid catalyst may be recycled or regenerated when used in a batch process or a continuous process.

The reaction conditions for the alkylation depend upon the type of catalyst used, and any suitable set of reaction conditions that result in high conversion to the alkylhydroxyaromatic product can be employed. Typically, the reaction temperature for the alkylation reaction will be in the range of about 25° C. to about 200° C. and preferably from about 40° C. to about 135° C. The reaction pressure will generally be atmospheric, although higher or lower pressures may be employed. The alkylation process can be practiced in a batchwise, continuous or semi-continuous manner. The molar ratio of the hydroxyaromatic compound to one or more olefins is normally in the range of about 0.5:1 to about 10:1, and preferably will be in the range of about 3:1 to about 5:1.

The alkylation reaction may be carried out neat or in the presence of a solvent which is inert to the reaction of the hydroxyaromatic compound and the olefin mixture. When employed, a typical solvent is hexane.

Upon completion of the reaction, the desired alkylhydroxyaromatic compound can be isolated using conventional techniques. Typically, excess hydroxyaromatic compound is distilled from the reaction product.

The alkyl group of the alkylhydroxyaromatic compound is typically attached to the hydroxyaromatic compound primarily in the ortho and para positions, relative to the hydroxyl group.

The alkyl-substituted hydroxyaromatic compound is subsequently sulfurized, neutralized and overbased in any order to provide an overbased salt of a sulfurized alkyl-substituted hydroxyaromatic composition. The sulfurization, neutralization and overbasing steps can be performed in any order so as to provide the overbased salt of the sulfurized alkyl-substituted hydroxyaromatic composition. Alternatively, the sulfurization and neutralization can be carried out simultaneously followed by the overbasing step.

In general, sulfurization is carried out by contacting the alkyl-substituted hydroxyaromatic compound with a sulfur source which introduces $S_x$ bridging groups between alkyl-substituted hydroxyaromatic compounds, wherein x is 1 to 7, in the presence of a base. Any suitable sulfur source can be used such as, for example, elemental sulfur or a halide thereof such as sulphur monochloride or sulphur dichloride, hydrogen sulfide, sulfur dioxide and sodium sulfide hydrates. The sulfur can be employed either as molten sulfur or as a solid (e.g., powder or particulate) or as a solid suspension in a compatible hydrocarbon liquid.

The base catalyzes the reaction to incorporate sulfur onto the alkylhydroxyaromatic compound. A suitable base includes, but is not limited to, NaOH, KOH, $Ca(OH)_2$ and the like and mixtures thereof.

The base is generally employed at from about 0.01 to about 1 mole percent to the alkyl-substituted hydroxyaromatic compound in the reaction system. In one embodiment, the base is employed at from about 0.01 to about 0.1 mole percent to the alkyl-substituted hydroxyaromatic compound in the reaction system. The base can be added to the reaction mixture as a solid or a liquid. In one preferred embodiment, the base is added as an aqueous solution.

Sulfur is generally employed at from about 0.5 to about 4 moles per mole of the alkyl-substituted hydroxyaromatic compound in the reaction system. In one embodiment, sulfur is employed at from about 0.8 to 2 moles per mole of the alkyl-substituted hydroxyaromatic compound. In one embodiment, sulfur is employed at from about 1 to 1.5 moles per mole of alkyl-substituted hydroxyaromatic compound.

The temperature range in which the sulfurization reaction is carried out is generally about 130° C. to about 200° C. In one embodiment, the temperature range is from about 150° C. to about 180° C. The reaction can be conducted under atmospheric pressure (or slightly lower) or at elevated pressures. During sulfurization a significant amount of by-product hydrogen sulfide gas is evolved. In one embodiment the reaction is carried out under vacuum to facilitate the $H_2S$ elimination. The exact pressure developed during the reaction is dependent upon such factors as the design and operation of the system, the reaction temperature, and the vapor pressure of the reactants and products and it may vary during the course of the reaction. In one embodiment, the process pressures are at atmospheric to about 20 mm Hg.

Neutralization of the sulfurized or unsulfurized alkyl-substituted hydroxyaromatic compound may be carried out in a continuous or batch process by any method known to a person skilled in the art. Numerous methods are known in the art to neutralize the sulfurized or unsulfurized alkyl-substituted hydroxyaromatic compounds and to produce basic phenates by incorporation of a source of base. In general, neutralization can be carried out by contacting the sulfurized or unsulfurized alkyl-substituted hydroxyaromatic compound with a metal base under reactive conditions, preferably in an inert-compatible liquid hydrocarbon diluent. If desired, the reaction can be conducted under an inert gas, typically nitrogen. The metal base may be added either in a single addition or in a plurality of additions at intermediate points during the reaction.

Suitable metal basic compounds include hydroxides, oxides or alkoxides of the metal such as (1) an alkali metal salt derived from a metal base selected from an alkali hydroxide, alkali oxide or an alkali alkoxide, or (2) an alkaline earth metal salt derived from a metal base selected from an alkaline earth hydroxide, alkaline earth oxide or alkaline earth alkoxide. Representative examples of metal basic compounds with hydroxide functionality include lithium hydroxide, potassium hydroxide, sodium hydroxide, magnesium hydroxide, calcium hydroxide, barium hydroxide, aluminum hydroxide and the like. Representative examples of metal basic compounds with oxide functionality include lithium oxide, magnesium oxide, calcium oxide, barium oxide and the like. In one embodiment, the alkaline earth metal base is slaked lime (calcium hydroxide), because of its handling convenience and cost versus, for example, calcium oxide.

Neutralization is typically conducted in a suitable solvent or diluent oil, such as toluene, xylene and commonly with a promoter such as an alcohol, e.g., a $C_1$ to $C_{16}$ alcohol, such as methanol, decyl alcohol, or 2-ethyl hexanol; a diol, e.g., $C_2$ to $C_4$ alkylene glycols, such as ethylene glycol; and/or carboxylic acids. Suitable diluent oils include naphthenic oils and mixed oils, e.g., paraffinic oils such as 100 neutral oil. The quantity of solvent or diluent oil used is such that the amount of solvent or oil in the final product constitutes from about 25% to about 65% by weight of the final product, preferably from about 30% to about 50%. For example, the source of alkaline earth metal is added in excess as a slurry (i.e., as a pre-mixture of source of an alkaline earth metal lime, solvent or diluent oil) and then reacted with the sulfurized or unsulfurized alkyl-substituted hydroxyaromatic compound.

The neutralization reaction between the metal base and the sulfurized or unsulfurized alkyl-substituted hydroxyaromatic compound is typically conducted at temperatures above room temperature (20° C.). In general, neutralization can be carried out at a temperature of between about 100° C. and about 150° C. The neutralization reaction itself should take place for a period of time of from about 5 to about 60 minutes. If desired, the neutralization reaction is carried out in the presence of a promoter such as ethylene glycol, formic acid, acetic acid, and the like and mixtures thereof.

Overbasing can be carried out either during or after one of the sulfurization and/or neutralization steps and by any method known by a person skilled in the art. Alternatively, sulfurization, neutralization and overbasing can be carried out simultaneously. In general, the overbasing is carried out by reaction with an acidic overbasing compound such as, for example, carbon dioxide or boric acid. In one embodiment, an overbasing process is by way of carbonation, i.e., a reaction with carbon dioxide. Such carbonation can be conveniently effected by addition of solvents such as aromatic solvents, alcohols or a polyols, typically an alkylene diol, e.g., ethylene glycol. Conveniently, the reaction is conducted by the simple expedient bubbling of gaseous carbon dioxide through the reaction mixture. Excess solvents and any water formed during the overbasing reaction can be conveniently removed by distillation either during or after the reaction.

In one embodiment, the overbasing reaction is carried out in a reactor by reacting the salt of the sulfurized alkyl-substituted hydroxyaromatic composition with a source of an alkaline earth metal such as lime (i.e., an alkaline earth metal hydroxide) in the presence of carbon dioxide, and in the presence of an aromatic solvent (e.g., xylene), and a hydrocarbyl alcohol such as methanol. Conveniently, the reaction is conducted by the simple expedient of bubbling gaseous carbon dioxide through the reaction mixture. The carbon dioxide is introduced over a period of about 1 hour to about 3 hours, at a temperature ranging from about 150° C. to about 200° C. The degree of overbasing may be controlled by the quantity of the source of an alkaline earth metal, carbon dioxide and the reactants added to the reaction mixture and the reaction conditions used during the carbonation process.

In another embodiment of the invention, the overbasing reaction can be carried out between 140° C. and 180° C. in presence of a polyol, typically an alkylene diol, e.g., ethylene glycol, and/or alkanols, e.g., $C_6$ to $C_{16}$ alkanols, such as decyl alcohols, 2-ethyl hexanol. Excess solvent and any water formed during the overbasing reaction can be conveniently removed by distillation either during or after the reaction.

The overbased salt of a sulfurized alkyl-substituted hydroxyaromatic composition has a TBN greater than about 250. In one embodiment, the overbased salt of a sulfurized alkyl-substituted hydroxyaromatic composition has a TBN of from about 250 and up to about 400.

In general, the resulting overbased salt of a sulfurized alkyl-substituted hydroxyaromatic composition contains some amount, by combined, mass, of unsulfurized alkyl-substituted hydroxyaromatic compound and its unsulfurized metal salt. As one skilled in the art would understand, the overbased salt of a sulfurized alkyl-substituted hydroxyaromatic composition can contain other components in addition to the unsulfurized alkyl-substituted hydroxyaromatic compound and its unsulfurized metal salt.

Step (b) of the process includes sparging, i.e. bubbling, the overbased salt of a sulfurized alkyl-substituted hydroxyaromatic composition with air at a temperature ranging from about 190° C. to about 250° C. As understood by those skilled in the art, a variety of techniques and devices can advantageously be used to sparge air into the overbased salt of a sulfurized alkyl-substituted hydroxyaromatic composition and is not limited to any specific technique or equipment. For example, air can be introduced into the overbased salt of a sulfurized alkyl-substituted hydroxyaromatic by using sparge tubes equipped with porous sintered elements to enable efficient contacting of air and liquid. Air/liquid contacting may also be promoted through the use of a gas dispersion impeller. Air sparging can be conducted under vacuum conditions, preferably anywhere from atmospheric to elevated pressures.

In general, sparging the overbased salt of a sulfurized alkyl-substituted hydroxyaromatic composition with air at a temperature ranging from about 190° C. to about 250° C. involves removing substantially all of the unsulfurized alkyl-substituted hydroxyaromatic compound and the unsulfurized metal salt of the alkyl-substituted hydroxyaromatic compound from the composition to provide a composition substantially free of the unsulfurized alkyl-substituted hydroxyaromatic compound and the unsulfurized metal salt of the alkyl-substituted hydroxyaromatic compound. The term "substantially free" as used herein means relatively low levels, if any, of the unsulfurized alkyl-substituted hydroxyaromatic compound and the unsulfurized metal salt of the alkyl-substituted hydroxyaromatic compound which remains after the step (b), e.g., less than about 1.5 wt. %, or less than about 0.3 wt. %. In one embodiment, the term "substantially free" ranges from about 0.1 to less than about 1.5 wt. %. In another embodiment, the term "substantially free" ranges from about 0.1 to less than about 1 wt. %. In another embodiment, the term "substantially free" ranges from about 0.1 to about 0.3 wt. %.

Lubricating Oil Composition

Another embodiment of the present invention is directed to a lubricating oil composition containing at least (a) a major amount of an oil of lubricating viscosity; and (b) a minor amount of an overbased salt of a sulfurized alkyl-substituted hydroxyaromatic composition which is prepared by the process comprising: (i) providing an overbased salt of a sulfurized alkyl-substituted hydroxyaromatic composition having a total base number greater than about 250; and (ii) sparging the overbased salt of a sulfurized alkyl-substituted hydroxyaromatic composition with air at a temperature ranging from about 190° C. to about 250° C.

Generally, the overbased salt of a sulfurized alkyl-substituted hydroxyaromatic composition of this invention will be present in the lubricating oil compositions in an amount ranging from about 0.001 wt. % to about 40 wt. %, based on the total weight of the lubricating oil composition.

The oil of lubricating viscosity for use in the lubricating oil compositions of this invention, also referred to as a base oil, is typically present in a major amount, e.g., an amount of greater than 50 wt. %, or greater than about 70 wt. %, or from about 80 to about 99.5 wt. % or from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered oil of lubricating viscosity used in formulating lubricating oil compositions for any and all such applications, e.g., engine oils, marine cylinder oils, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (°C.). In one embodiment, the base oil is a marine oil having a viscosity of about 30 to about 35 cSt at 100° C. (bright stock). In another embodiment, the base oil is a marine oil having a viscosity of about 4 to about 12 cSt range). In another embodiment, the base oil is a monograde base oil, e.g., a base oil having a SAE Viscosity Grade of 20, 30, 40 or 50.

In another embodiment, the base oil is an engine oil having a kinematic viscosity range at 100° C. of about 2 cSt to about 30 cSt, or from about 3 cSt to about 16 cSt, or from about 4 cSt to about 12 cSt and will be selected or blended depending on the desired end use and the additives in the finished oil to give the desired grade of engine oil, e.g., a lubricating oil composition having an SAE Viscosity Grade of 0 W, 0 W-20, O W-30, O W-40, 0 W-50, 0 W-60, 5 W, 5 W-20, 5 W-30, 5 W-40, 5 W-50, 5 W-60, 10 W, 10 W-20, 10 W-30, 10 W-40, 10 W-50, 15 W, 15 W-20, 15 W-30 or 15 W-40. Oils used as gear oils can have viscosities ranging from about 2 cSt to about 2000 cSt at 100° C. The kinematic viscosity of the base oils or the lubricating oil compositions disclosed herein can be measured according to ASTM D 445, which is incorporated herein by reference.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition,, Addendum I, December 1998. Group IV base oils are polyalphaolefins (PAO). Group V base oils include all other base oils not included in Group I, II, III, or IV.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenens, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$ oxo acid diester of tetraetylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetracthylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The lubricating oil compositions of the present invention may also contain other conventional additives that can impart or improve any desirable property of the lubricating oil composition in which these additives are dispersed or dissolved. Any additive known to a person of ordinary skill in the art may be used in the lubricating oil compositions disclosed herein. Some suitable additives have been described in Mortier et al., "Chemistry and Technology of Lubricants," 2nd Edition, London, Springer, (1996); and Leslie R. Rudnick, "Lubricant Additives: Chemistry and Applications," New York, Marcel Dekker (2003), both of which are incorporated herein by reference. For example, the lubricating oil compositions can be blended with antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. A variety of the additives are known and commercially available. These additives, or their analogous compounds, can be employed for the preparation of the lubricating oil compositions of the invention by the usual blending procedures.

In general, the concentration of each of the additives in the lubricating oil composition, when used, may range from about 0.001 wt. % to about 20 wt. %, from about 0.01 wt. % to about 15 wt. %, or from about 0.1 wt. % to about 10 wt. %, based on the total weight of the lubricating oil composition.

The lubricating oil composition disclosed herein can contain one or more antioxidants that can reduce or prevent the oxidation of the base oil. Any antioxidant known by a person of ordinary skill in the art may be used in the lubricating oil composition. Non-limiting examples of suitable antioxidants include amine-based antioxidants (e.g., alkyl diphenylamines such as bis-nonylated diphenylamine, bis-octylated diphenylamine, and octylated/butylated diphenylamine, phenyl-$\alpha$-naphthylamine, alkyl or arylalkyl substituted phenyl-$\alpha$-naphthylamine, alkylated p-phenylene diamines, tetramethyl-diaminodiphenylamine and the like), phenolic antioxidants (e.g., 2-tert-butylphenol, 4-methyl-2,6-di-tert-butylphenol, 2,4,6-tri-tert-butylphenol, 2,6-di-tert-butyl-p-cresol, 2,6-di-tert-butylphenol, 4,4'-methylenebis-(2,6-di-tert-butylphenol), 4,4'-thiobis(6-di-tert-butyl-o-cresol) and the like), sulfur-based antioxidants (e.g., dilauryl-3,3'-thiodipropionate, sulfurized phenolic antioxidants and the like), phosphorous-based antioxidants (e.g., phosphites and the like), zinc dithiophosphate, oil-soluble copper compounds and combinations thereof. The amount of the antioxidant may vary from about 0.01 wt. % to about 10 wt. %, from about 0.05 wt. % to about 5 wt. %, or from about 0.1 wt. % to about 3 wt. %, based on the total weight of the lubricating oil composition. Some suitable antioxidants have been described in Leslie R. Rudnick, "Lubricant Additives: Chemistry and Applications," New York, Marcel Dekker, Chapter 1, pages 1-28 (2003), which is incorporated herein by reference.

The lubricating oil composition disclosed herein can contain one or more ashless dispersant compounds to maintain in suspension insoluble materials resulting from oxidation during use, thus preventing sludge flocculation and precipitation or deposition on metal parts. Dispersants may also function to reduce changes in lubricating oil viscosity by preventing the growth of large contaminant particles in the lubricant. Any dispersant known by a person of ordinary skill in the art may be used in the lubricating oil composition. An ashless dispersant generally comprises an oil soluble polymeric hydrocarbon backbone having functional groups that are capable of associating with particles to be dispersed.

In one embodiment, an ashless dispersant is one or more basic nitrogen-containing ashless dispersants. Nitrogen-containing basic ashless (metal-free) dispersants contribute to the base number or BN (as can be measured by ASTM D 2896) of a lubricating oil composition to which they are added, without introducing additional sulfated ash. Basic nitrogen-containing ashless dispersants useful in this invention include hydrocarbyl succinimides; hydrocarbyl succinamides; mixed ester/amides of hydrocarbyl-substituted succinic acids formed by reacting a hydrocarbyl-substituted succinic acylating agent stepwise or with a mixture of alcohols and amines, and/or with amino alcohols; Mannich condensation products of hydrocarbyl-substituted phenols, formaldehyde and polyamines; and amine dispersants formed by reacting high molecular weight aliphatic or alicyclic halides with amines, such as polyalkylene polyamines. Mixtures of such dispersants can also be used.

Representative examples of ashless dispersants include, but are not limited to, amines, alcohols, amides, or ester polar moieties attached to the polymer backbones via bridging groups. An ashless dispersant may be, for example, selected from oil soluble salts, esters, amino-esters, amides, imides, and oxazolines of long chain hydrocarbon substituted mono and dicarboxylic acids or their anhydrides; thiocarboxylate derivatives of long chain hydrocarbons, long chain aliphatic hydrocarbons having a polyamine attached directly thereto;

and Mannich condensation products formed by condensing a long chain substituted phenol with formaldehyde and polyalkylene polyamine.

Carboxylic dispersants are reaction products of carboxylic acylating agents (acids, anhydrides, esters, etc.) comprising at least about 34 and preferably at least about 54 carbon atoms with nitrogen containing compounds (such as amines), organic hydroxy compounds (such as aliphatic compounds including monohydric and polyhydric alcohols, or aromatic compounds including phenols and naphthols), and/or basic inorganic materials. These reaction products include imides, amides, and esters.

Succinimide dispersants are a type of carboxylic dispersant. They are produced by reacting hydrocarbyl-substituted succinic acylating agent with organic hydroxy compounds, or with amines comprising at least one hydrogen atom attached to a nitrogen atom, or with a mixture of the hydroxy compounds and amines. The term "succinic acylating agent" refers to a hydrocarbon-substituted succinic acid or a succinic acid-producing compound, the latter encompasses the acid itself. Such materials typically include hydrocarbyl-substituted succinic acids, anhydrides, esters (including half esters) and halides.

Succinic-based dispersants have a wide variety of chemical structures. One class of succinic-based dispersants may be represented by the formula:

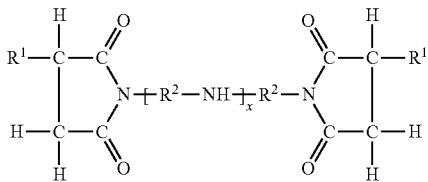

wherein each $R^1$ is independently a hydrocarbyl group, such as a polyolefin-derived group. Typically the hydrocarbyl group is an alkyl group, such as a polyisobutyl group. Alternatively expressed, the $R^1$ groups can contain about 40 to about 500 carbon atoms, and these atoms may be present in aliphatic forms. $R^2$ is an alkylene group, commonly an ethylene ($C_2H_4$) group. Examples of succinimide dispersants include those described in, for example, U.S. Pat. Nos. 3,172,892, 4,234,435 and 6,165,235.

The polyalkenes from which the substituent groups are derived are typically homopolymers and interpolymers of polymerizable olefin monomers of 2 to about 16 carbon atoms, and usually 2 to 6 carbon atoms. The amines which are reacted with the succinic acylating agents to form the carboxylic dispersant composition can be monoamines or polyamines.

Succinimide dispersants are referred to as such since they normally contain nitrogen largely in the form of imide functionality, although the amide functionality may be in the form of amine salts, amides, imidazolines as well as mixtures thereof. To prepare a succinimide dispersant, one or more succinic acid-producing compounds and one or more amines are heated and typically water is removed, optionally in the presence of a substantially inert organic liquid solvent/diluent. The reaction temperature can range from about 80° C. up to the decomposition temperature of the mixture or the product, which typically falls between about 100° C. to about 300° C. Additional details and examples of procedures for preparing the succinimide dispersants of the present invention include those described in, for example, U.S. Pat. Nos. 3,172,892, 3,219,666, 3,272,746, 4,234,435, 6,165,235 and 6,440,905.

Suitable ashless dispersants may also include amine dispersants, which are reaction products of relatively high molecular weight aliphatic halides and amines, preferably polyalkylene polyamines. Examples of such amine dispersants include those described in, for example, U.S. Pat. Nos. 3,275,554, 3,438,757, 3,454,555 and 3,565,804.

Suitable ashless dispersants may further include "Mannich dispersants," which are reaction products of alkyl phenols in which the alkyl group contains at least about 30 carbon atoms with aldehydes (especially formaldehyde) and amines (especially polyalkylene polyamines). Examples of such dispersants include those described in, for example, U.S. Pat. Nos. 3,036,003, 3,586,629, 3,591,598 and 3,980,569.

Suitable ashless dispersants may also be post-treated ashless dispersants such as post-treated succinimides, e.g., post-treatment processes involving borate or ethylene carbonate as disclosed in, for example, U.S. Pat. Nos. 4,612,132 and 4,746,446; and the like as well as other post-treatment processes. The carbonate-treated alkenyl succinimide is a polybutene succinimide derived from polybutenes having a molecular weight of about 450 to about 3000, preferably from about 900 to about 2500, more preferably from about 1300 to about 2400, and most preferably from about 2000 to about 2400, as well as mixtures of these molecular weights. Preferably, it is prepared by reacting, under reactive conditions, a mixture of a polybutene succinic acid derivative, an unsaturated acidic reagent copolymer of an unsaturated acidic reagent and an olefin, and a polyamine, such as disclosed in U.S. Pat. No. 5,716,912, the contents of which are incorporated herein by reference.

Suitable ashless dispersants may also be polymeric, which are interpolymers of oil-solubilizing monomers such as decyl methacrylate, vinyl decyl ether and high molecular weight olefins with monomers containing polar substitutes. Examples of polymeric dispersants include those described in, for example, U.S. Pat. Nos. 3,329,658; 3,449,250 and 3,666,730.

In one preferred embodiment of the present invention, an ashless dispersant for use in the lubricating oil composition is a bis-succinimide derived from a polyisobutenyl group having a number average molecular weight of about 700 to about 2300.

The lubricating oil composition disclosed herein can contain an additional detergent other than the overbased salt of a sulfurized alkyl-substituted hydroxyaromatic composition of this invention. Any compound or a mixture of compounds that can reduce or slow the build up of engine deposits can be used as a detergent. Non-limiting examples of suitable metal detergent include sulfurized or unsulfurized alkyl or alkenyl phenates, alkyl or alkenyl aromatic sulfonates, borated sulfonates, sulfurized or unsulfurized metal salts of multi-hydroxy alkyl or alkenyl aromatic compounds, alkyl or alkenyl hydroxy aromatic sulfonates, sulfurized or unsulfurized alkyl or alkenyl naphthenates, metal salts of alkanoic acids, metal salts of an alkyl or alkenyl multiacid, and chemical and physical mixtures thereof. Other non-limiting examples of suitable metal detergents include metal sulfonates, salicylates, phosphonates, thiophosphonates and combinations thereof. The metal can be any metal suitable for making sulfonate, salicylate or phosphonate detergents. Non-limiting examples of suitable metals include alkali metals, alkaline metals and transition metals. In some embodiments, the metal is Ca, Mg, Ba, K, Na, Li or the like.

Generally, the amount of the additional detergent can be from about 0.001 wt. % to about 25 wt. %, from about 0.05 wt. % to about 20 wt. %, or from about 0.1 wt. % to about 15 wt. %, based on the total weight of the lubricating oil composition. Some suitable detergents have been described in Mortier et al., "Chemistry and Technology of Lubricants," 2nd Edition, London, Springer, Chapter 3, pages 75-85 (1996); and Leslie R. Rudnick, "Lubricant Additives: Chemistry and Applications," New York, Marcel Dekker, Chapter 4, pages 113-136 (2003), both of which are incorporated herein by reference.

The lubricating oil composition disclosed herein can contain one or more friction modifiers that can lower the friction between moving parts. Any friction modifier known by a person of ordinary skill in the art may be used in the lubricating oil composition. Non-limiting examples of suitable friction modifiers include fatty carboxylic acids; derivatives (e.g., alcohol, esters, borated esters, amides, metal salts and the like) of fatty carboxylic acid; mono-, di- or tri-alkyl substituted phosphoric acids or phosphonic acids; derivatives (e.g., esters, amides, metal salts and the like) of mono-, di- or tri-alkyl substituted phosphoric acids or phosphonic acids; mono-, di- or tri-alkyl substituted amines; mono- or di-alkyl substituted amides and combinations thereof. In some embodiments examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, or a $C_6$ to $C_{24}$, or a $C_6$ to $C_{20}$, fatty acid ester and a nitrogen-containing compound selected from the group consisting of ammonia, and an alkanolamine and the like and mixtures thereof. The amount of the friction modifier may vary from about 0.01 wt. % to about 10 wt. %, from about 0.05 wt. % to about 5 wt. %, or from about 0.1 wt. % to about 3 wt. %, based on the total weight of the lubricating oil composition. Some suitable friction modifiers have been described in Mortier et al., "Chemistry and Technology of Lubricants," 2nd Edition, London, Springer, Chapter 6, pages 183-187 (1996); and Leslie R. Rudnick, "Lubricant Additives: Chemistry and Applications," New York, Marcel Dekker, Chapters 6 and 7, pages 171-222 (2003), both of which are incorporated herein by reference.

The lubricating oil composition disclosed herein can contain one or more anti-wear agents that can reduce friction and excessive wear. Any anti-wear agent known by a person of ordinary skill in the art may be used in the lubricating oil composition. Non-limiting examples of suitable anti-wear agents include zinc dithiophosphate, metal (e.g., Pb, Sb, Mo and the like) salts of dithiophosphates, metal (e.g., Zn, Pb, Sb, Mo and the like) salts of dithiocarbamates, metal (e.g., Zn, Pb, Sb and the like) salts of fatty acids, boron compounds, phosphate esters, phosphite esters, amine salts of phosphoric acid esters or thiophosphoric acid esters, reaction products of dicyclopentadiene and thiophosphoric acids and combinations thereof. The amount of the anti-wear agent may vary from about 0.01 wt. % to about 5 wt. %, from about 0.05 wt. % to about 3 wt. %, or from about 0.1 wt. % to about 1 wt. %, based on the total weight of the lubricating oil composition. Some suitable anti-wear agents have been described in Leslie R. Rudnick, "Lubricant Additives: Chemistry and Applications," New York, Marcel Dekker, Chapter 8, pages 223-258 (2003), which is incorporated herein by reference.

In certain embodiments, the anti-wear agent is or comprises a dihydrocarbyl dithiophosphate metal salt, such as zinc dialkyl dithiophosphate compounds. The metal of the dihydrocarbyl dithiophosphate metal salt may be an alkali or alkaline earth metal, or aluminum, lead, tin, molybdenum, manganese, nickel or copper. In some embodiments, the metal is zinc. In other embodiments, the alkyl group of the dihydrocarbyl dithiophosphate metal salt has from about 3 to about 22 carbon atoms, from about 3 to about 18 carbon atoms, from about 3 to about 12 carbon atoms, or from about 3 to about 8 carbon atoms. In further embodiments, the alkyl group is linear or branched.

The amount of the dihydrocarbyl dithiophosphate metal salt including the zinc dialkyl dithiophosphate salts in the lubricating oil composition disclosed herein is measured by its phosphorus content. In some embodiments, the phosphorus content of the lubricating oil composition disclosed herein is from about 0.01 wt. % to about 0.14 wt., based on the total weight of the lubricating oil composition.

The lubricating oil composition disclosed herein can contain one or more foam inhibitors or anti-foam inhibitors that can break up foams in oils. Any foam inhibitor or anti-foam known by a person of ordinary skill in the art may be used in the lubricating oil composition. Non-limiting examples of suitable foam inhibitors or anti-foam inhibitors include silicone oils or polydimethylsiloxanes, fluorosilicones, alkoxylated aliphatic acids, polyethers (e.g., polyethylene glycols), branched polyvinyl ethers, alkyl acrylate polymers, alkyl methacrylate polymers, polyalkoxyamines and combinations thereof. In some embodiments, the foam inhibitors or anti-foam inhibitors comprises glycerol monostearate, polyglycol palmitate, a trialkyl monothiophosphate, an ester of sulfonated ricinoleic acid, benzoylacetone, methyl salicylate, glycerol monooleate, or glycerol dioleate. The amount of the foam inhibitors or anti-foam inhibitors may vary from about 0.001 wt. % to about 5 wt. %, from about 0.05 wt. % to about 3 wt. %, or from about 0.1 wt. % to about 1 wt. %, based on the total weight of the lubricating oil composition. Some suitable foam inhibitors or anti-foam inhibitors have been described in Mortier et al., "Chemistry and Technology of Lubricants," 2nd Edition, London, Springer, Chapter 6, pages 190-193 (1996), which is incorporated herein by reference.

The lubricating oil composition disclosed herein can contain one or more pour point depressants that can lower the pour point of the lubricating oil composition. Any pour point depressant known by a person of ordinary skill in the art may be used in the lubricating oil composition. Non-limiting examples of suitable pour point depressants include polymethacrylates, alkyl acrylate polymers, alkyl methacrylate polymers, di(tetra-paraffin phenol)phthalate, condensates of tetra-paraffin phenol, condensates of a chlorinated paraffin with naphthalene and combinations thereof. In some embodiments, the pour point depressant comprises an ethylene-vinyl acetate copolymer, a condensate of chlorinated paraffin and phenol, polyalkyl styrene or the like. The amount of the pour point depressant may vary from about 0.01 wt. % to about 10 wt. %, from about 0.5 wt. % to about 5 wt. %, or from about 0.1 wt. % to about 3 wt. %, based on the total weight of the lubricating oil composition. Some suitable pour point depressants have been described in Mortier et al., "Chemistry and Technology of Lubricants," 2nd Edition, London, Springer, Chapter 6, pages 187-189 (1996); and Leslie R. Rudnick, "Lubricant Additives: Chemistry and Applications," New York, Marcel Dekker, Chapter 11, pages 329-354 (2003), both of which are incorporated herein by reference.

In one embodiment, the lubricating oil composition disclosed herein does not contain one or more demulsifiers. In another embodiment, the lubricating oil composition disclosed herein can contain one or more demulsifiers that can promote oil-water separation in lubricating oil compositions that are exposed to water or steam. Any demulsifier known by a person of ordinary skill in the art may be used in the lubricating oil composition. Non-limiting examples of suitable demulsifiers include anionic surfactants (e.g., alkylnaphthalene sulfonates, alkyl benzene sulfonates and the like), nonionic alkoxylated alkyl phenol resins, polymers of alkylene oxides (e.g., polyethylene oxide, polypropylene oxide, block copolymers of ethylene oxide, propylene oxide and the like), esters of oil soluble acids, polyoxyethylene sorbitan ester and combinations thereof. The amount of the demulsifier may vary from about 0.01 wt. % to about 10 wt. %, from about 0.05 wt. % to about 5 wt. %, or from about 0.1 wt. % to about 3 wt. %, based on the total weight of the lubricating oil composition. Some suitable demulsifiers have been described in Mortier et al., "Chemistry and Technology of Lubricants," 2nd Edition, London, Springer, Chapter 6, pages 190-193 (1996), which is incorporated herein by reference.

The lubricating oil composition disclosed herein can contain one or more corrosion inhibitors that can reduce corrosion. Any corrosion inhibitor known by a person of ordinary skill in the art may be used in the lubricating oil composition. Non-limiting examples of suitable corrosion inhibitor include half esters or amides of dodecylsuccinic acid, phosphate esters, thiophosphates, alkyl imidazolines, sarcosines and combinations thereof. The amount of the corrosion inhibitor may vary from about 0.01 wt. % to about 5 wt. %, from about 0.05 wt. % to about 3 wt. %, or from about 0.1 wt. % to about 1 wt. %, based on the total weight of the lubricating oil composition. Some suitable corrosion inhibitors have been described in Mortier et al., "Chemistry and Technology of Lubricants," 2nd Edition, London, Swinger, Chapter 6, pages 193-196 (1996), which is incorporated herein by reference.

The lubricating oil composition disclosed herein can contain one or more extreme pressure (EP) agents that can prevent sliding metal surfaces from seizing under conditions of extreme pressure. Any extreme pressure agent known by a person of ordinary skill in the art may be used in the lubricating oil composition. Generally, the extreme pressure agent is a compound that can combine chemically with a metal to form a surface film that prevents the welding of asperities in opposing metal surfaces under high loads. Non-limiting examples of suitable extreme pressure agents include sulfurized animal or vegetable fats or oils, sulfurized animal or vegetable fatty acid esters, fully or partially esterified esters of trivalent or pentavalent acids of phosphorus, sulfurized olefins, dihydrocarbyl polysulfides, sulfurized Diels-Alder adducts, sulfurized dicyclopentadiene, sulfurized or co-sulfurized mixtures of fatty acid esters and monounsaturated olefins, co-sulfurized blends of fatty acid, fatty acid ester and alpha-olefin, functionally-substituted dihydrocarbyl polysulfides, thia-aldehydes, thia-ketones, epithio compounds, sulfur-containing acetal derivatives, co-sulfurized blends of terpene and acyclic olefins, and polysulfide olefin products, amine salts of phosphoric acid esters or thiophosphoric acid esters and combinations thereof. The amount of the extreme pressure agent may vary from about 0.01 wt. % to about 5 wt. %, from about 0.05 wt. % to about 3 wt. %, or from about 0.1 wt. % to about 1 wt. %, based on the total weight of the lubricating oil composition. Some suitable extreme pressure agents have been described in Leslie R. Rudnick, "Lubricant Additives: Chemistry and Applications," New York, Marcel Dekker, Chapter 8, pages 223-258 (2003), which is incorporated herein by reference.

The lubricating oil composition disclosed herein can contain one or more rust inhibitors that can inhibit the corrosion of ferrous metal surfaces. Any rust inhibitor known by a person of ordinary skill in the art may be used in the lubricating oil composition. Non-limiting examples of suitable rust inhibitors include nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof. The amount of the rust inhibitor may vary from about 0.01 wt. % to about 10 wt. %, from about 0.05 wt. % to about 5 wt. %, or from about 0.1 wt. % to about 3 wt. %, based on the total weight of the lubricating oil composition.

The lubricating oil composition disclosed herein can contain one or more multifunctional additives. Non-limiting examples of suitable multifunctional additives include sulfurized oxymolybdenum dithiocarbamate, sulfurized oxymolybdenum organophosphorodithioate, oxymolybdenum monoglyceride, oxymolybdenum dietylate amide, amine-molybdenum complex compound, and sulfur-containing molybdenum complex compound.

The lubricating oil composition disclosed herein can contain one or more viscosity index improvers. Non-limiting examples of suitable viscosity index improvers include polymethacrylate type polymers, ethylene-propylene copolymers, styrene-isoprene copolymers, hydrated styrene-isoprene copolymers, polyisobutylene, and dispersant type viscosity index improvers.

The lubricating oil composition disclosed herein can contain one or more metal deactivators. Non-limiting examples of suitable metal deactivators include disalicylidene propylenediamine, triazole derivatives, thiadiazole derivatives, and mercaptobenzimidazoles.

If desired, the overbased salt of a sulfurized alkyl-substituted hydroxyaromatic composition of this invention may be provided as an additive package or concentrate in which the overbased salt of a sulfurized alkyl-substituted hydroxyaromatic composition of this invention optionally with the foregoing lubricant additives are incorporated into a substantially inert, normally liquid organic diluent such as, for example, mineral oil, naphtha, benzene, toluene or xylene to form an additive concentrate. These concentrates usually contain from about 20% to about 80% by weight of such diluent. Typically, a neutral oil having a viscosity of about 4 to about 8.5 cSt at 100° C. and preferably about 4 to about 6 cSt at 100° C. will be used as the diluent, though synthetic oils, as well as other organic liquids which are compatible with the additives and finished lubricating oil can also be used. The additive package will typically contain one or more of the various additives, referred to above, in the desired amounts and ratios to facilitate direct combination with the requisite amount of the oil of lubricating viscosity.

The lubricating oil composition disclosed herein may be suitable for use as motor oils (or engine oils or crankcase oils), marine diesel engine lubricating oil compositions, and the like.

In one embodiment, the lubricating oil composition disclosed herein is a motor or engine oil. Such a motor oil composition may be used to lubricate all major moving parts in any reciprocating internal combustion engine, reciprocating compressors and in steam engines of crankcase design. In automotive applications, the motor oil composition may also be used to cool hot engine parts, keep the engine free of rust and deposits, and seal the rings and valves against leakage of combustion gases. The motor oil composition may comprise a base oil, an overbased salt of a sulfurized alkyl-substituted hydroxyaromatic composition of the present invention, and one or more optional additives.

In one embodiment, the lubricating oil composition disclosed herein is a marine engine oil. Such a marine engine oil composition may be used to lubricate a marine engine such as two-stroke crosshead marine (Marine Cylinder Lubricant) engines or so-called trunk piston engine oil (TPEO) engines, i.e. semi-rapid four-stroke engines, operating with heavy fuel. The marine engine oil composition may comprise a base oil, an overbased salt of a sulfurized alkyl-substituted hydroxyaromatic composition as disclosed herein, and one or more optional additives.

The following non-limiting examples are illustrative of the present invention.

The concentration of total free unsulfurized alkylhydroxyaromatic compound and its unsulfurized metal salts (i.e., "total TPP" or "total residual TPP") in the salt of a sulfurized alkyl-substituted hydroxyaromatic composition as disclosed herein and exemplified below, as well as lubricants and oil additives containing salts of a sulfurized alkyl-substituted hydroxyaromatic composition is determined by reverse phase High Performance Liquid Chromatography (HPLC). In the HPLC method, samples were prepared for analysis by weighing accurately 80 to 120 mg of sample into a 10 ml volumetric flask, diluting to the level mark with methylene chloride, and mixing until the sample is fully dissolved.

The HPLC system used in the HPLC method included a HPLC pump, a thermostatted HPLC column compartment, HPLC fluorescence detector, and PC-based chromatography data acquisition system. The particular system described is based on an Agilent 1200 HPLC with ChemStation software. The HPLC column was a Phenomenex Luna C8(2) 150×4.6 mm 5 μm 100 Å, P/N 00F4249E0.

The following system settings were used in performing the analyses:
Pump flow=1.0 ml/min
Maximum pressure=200 bars
Fluorescence wavelength: 225 excitation 313 emission: Gain=9
Column Thermostat temperature=25C
Injection Size=1 μL of diluted sample
Elution type: Gradient, reverse phase
Gradient: 0-7 min 85/15 methanol/water switching to 100% methanol linear gradient.
Run time: 17 minutes The resulting chromatogram typically contains several peaks. Peaks due to the free unsulfurized alkylhydroxyaromatic compound typically elute together at early retention times; whereas peaks due to sulfurized salts of alkylhydroxyaromatic compounds typically elute at longer retention times. For purposes of quantitation, the area of the single largest peak of the free unsulfurized alkylhydroxyaromatic compound and its unsulfurized metal salt was measured, and then that area was used to determine the concentration of the total free unsulfurized alkylhydroxyaromatic compound and its unsulfurized metal salt species. The assumption is that the speciation of alkylhydroxyaromatic compounds does not change; if something does change the speciation of the alkylhydroxyaromatic compounds, then recalibration is necessary.

The area of the chosen peak is compared to a calibration curve to arrive at the wt. % of free alkylphenol and free unsulfurized salts of alkylphenols. The calibration curve was developed using the same peak in the chromatogram obtained for the free unsulfurized alkylhydroxyaromatic compound used to make the phenate product.

The tendency of marine lubricants to resist oxidation which can lead to, for example, a decrease in Total Base Number during use, can be evaluated using the Modified Institute of Petroleum 48 (MIP-48) Test MIP-48.

Modified Institute of Petroleum 48 (MIP-48) Test

This test measures the degree of stability against oxidation-based viscosity increase of the lubricant. The test consists of a thermal and an oxidative part. During both parts of the test the test samples are heated for a period of time. In the thermal part of the test, nitrogen is passed through a heated oil sample for 24 hours and in parallel during the oxidative part of the test, air is passed through a heated oil sample for 24 hours. The two samples were then cooled, and the viscosities of the samples were determined. The BN depletion and viscosity increase of the test oil caused by oxidation are determined and corrected for the thermal effect. The oxidation-based viscosity increase for each marine system oil composition was calculated by subtracting the kinematic viscosity at 100° C. for the nitrogen-blown sample from the kinematic viscosity at 100° C. for the air-blown sample, and dividing the subtraction product by the kinematic viscosity at 100° C. for the nitrogen blown sample.

COMPARATIVE EXAMPLE A

Preparation of Basic Sulfurized Carbonated Calcium Alkyl Phenate Without Sparging A slurry of an alkylphenol wherein the alkyl radical was derived from a polypropylene having an average of 12 carbon atoms, base oil, fluorine-containing silicon foam inhibitor, and lime are added to a reactor. The slurry was heated to 120° C. and sulfonic acid is added. Sulfur is slowly added to the reactor at about 130° C., and at about 150° C. decyl alcohol and ethylene glycol were added slowly to the reactor which was kept at about 150-155° C. for the entire addition. The reaction mixture was then heated to about 175° C. and another aliquot of ethylene glycol was added while simultaneously sparging $CO_2$. After carbonation, the mixture was heated to about 230° C. and vacuum applied to remove water, ethylene glycol, and decyl alcohol. The phenate had 5.7 wt. % of residual total TPP, determined by HPLC method. Additional lube oil was blended in to achieve a diluted detergent additive as characterized below in Table 1.

TABLE 1

| | |
|---|---|
| TBN, mg KOH/g | 263 |
| Vis @ 100° C. (cSt) | 308 |
| Ca (wt %) | 9.63 |
| S (wt %) | 3.21 |
| S/Ca | 0.33 |

COMPARATIVE EXAMPLE B

Preparation of Basic Sulfurized Carbonated Calcium Alkyl Phenate By Air Sparging.

Approximately 3000 grams of the basic sulfurized carbonated calcium alkyl phenate of Comparative Example A was added to a 4 liter reactor fitted with an external heating mantle and a sparge tube. The phenate was then heated to 160° C. as fast as possible. After reaching 160° C., air was added to the reactor thru the sparge tube at a rate of 0.5 grams/min. Air was sparged into the phenate for a period of 24 hours. The resulting phenate had 4.2 wt. % of residual total TPP, determined by HPLC method.

EXAMPLE 1

Preparation of Basic Sulfurized Carbonated Calcium Alkyl Phenate By Air Sparging.

Approximately 3000 grams of the basic sulfurized carbonated calcium alkyl phenate of Comparative Example A was added to a 4 liter reactor fitted with an external heating mantle and a sparge tube. The phenate was then heated to 202° C. as fast as possible. After reaching 202° C., air was added to the reactor thru the sparge tube at a rate of 0.5 grams/min. Air was sparged into the phenate for a period of 24 hours. The resulting phenate had 1.1 wt. % of residual total TPP, determined by HPLC method.

COMPARATIVE EXAMPLE C AND EXAMPLE 2

The following lubricating oil compositions were prepared using components and amounts as set forth below in Table 2. The additive components and amounts were the same for each of the examples. The lubricating oil compositions were evaluated using the MIP-48 test.

TABLE 2

| Components | Units | Comp. Ex. C | Ex. 2 |
|---|---|---|---|
| Comp. Ex. A | [m %] | 9.30 | — |
| Example 1 | [m %] | — | 9.10 |
| Other Additives | | | |
| Detergent(s) | [m %] | 10.70 | 10.70 |
| Dispersant | [m %] | 1.50 | 1.50 |
| Foam inhibitor | [m %] | 0.04 | 0.04 |
| ExxonMobil CORE ® 600N | [m %] | 54.48 | 54.41 |
| ExxonMobil CORE ® 2500BS | [m %] | 23.98 | 24.25 |
| Total Amount | [m %] | 100.00 | 100.00 |
| TBN | [mgKOH/g] | 68.6 | 68.5 |
| Viscosity (at 100° C.) | [cSt] | 20.03 | 20.47 |
| MIP-48 Test Result, Viscosity Increase | [%] | 26.5 | 18.9 |

COMPARATIVE EXAMPLE D AND EXAMPLE 3

The following lubricating oil compositions were prepared using components and amounts as set forth below in Table 3. The additive components and amounts were the same for each of the examples. The lubricating oil compositions were evaluated using the MIP-48 test.

TABLE 3

| Components | Units | Comp. Ex. D | Ex. 3 |
|---|---|---|---|
| Comp. Ex. A | [m %] | 1.70 | — |
| Example 1 | [m %] | — | 1.70 |
| Other Additives | | | |
| Detergent(s) | [m %] | 1.69 | 1.69 |
| Dispersant | [m %] | 0.87 | 0.87 |
| Antiwear Agent | [m %] | 0.44 | 0.44 |
| Foam inhibitor | [m %] | 0.03 | 0.03 |
| ExxonMobil CORE ® 600N | [m %] | 84.66 | 84.66 |
| ExxonMobil CORE ® 2500BS | [m %] | 10.61 | 10.61 |
| Total Amount | [m %] | 100.00 | 100.00 |
| TBN | [mgKOH/g] | 9.0 | 9.2 |
| Viscosity (at 100° C.) | [cSt] | 14.08 | 14.17 |
| MIP-48 Test Result, Viscosity Increase | [%] | 58.9 | 41.0 |

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A process for preparing an overbased salt of a sulfurized alkyl-substituted hydroxyaromatic composition comprising:
    (a) providing an overbased salt of a sulfurized alkyl-substituted hydroxyaromatic composition having a total base number (TBN) greater than about 250; and
    (b) sparging the overbased salt of a sulfurized alkyl-substituted hydroxyaromatic composition with air at a temperature ranging from about 190° C. to about 250° C.

2. The process of claim 1, wherein the salt of a sulfurized alkyl-substituted hydroxyaromatic composition is produced by (i) alkylating a hydroxyaromatic compound with one or more normal alpha olefins; and (ii) sulfurizing, neutralizing and overbasing the alkyl-substituted hydroxyaromatic compound in any order.

3. The process of claim 2, wherein the hydroxyaromatic compound is a phenol and the alkyl-substituted hydroxyaromatic compound is derived from alkylation of the hydroxyaromatic compound with $C_9$ to $C_{18}$ oligomers of monomers selected from propylene, butylene or mixtures thereof.

4. The process of claim 1, wherein the overbased salt of a sulfurized alkyl-substituted hydroxyaromatic composition having a TBN greater than about 250 is an overbased salt of a sulfurized alkyl-substituted hydroxyaromatic composition having a TBN greater than about 250 and up to about 450.

5. The process of claim 1, wherein the step of sparging is conducted under vacuum.

6. The process of claim 1, wherein the step of sparging is conducted under pressure.

7. The process of claim 1, wherein the resulting overbased salt of a sulfurized alkyl-substituted hydroxyaromatic composition is substantially free of an unsulfurized substituted hydroxyaromatic compound and its metal salt.

8. The process of claim 1, wherein the resulting overbased salt of a sulfurized alkyl-substituted hydroxyaromatic composition contains less than about 1.5 wt. % of an unsulfurized alkyl-substituted hydroxyaromatic compound and its metal salt.

9. The process of claim 1, wherein the resulting overbased salt of a sulfurized alkyl-substituted hydroxyaromatic composition contains less than about 0.3 wt. % of an unsulfurized alkyl-substituted hydroxyaromatic compound and its metal salt.

* * * * *